(12) United States Patent
Malik et al.

(10) Patent No.: US 6,548,706 B2
(45) Date of Patent: Apr. 15, 2003

(54) PREPARATION OF 2S,3S-N-ISOBUTYL-N-(2-HYDROXY-3-AMINO-4-PHENYLBUTYL) -P-NITROBENZENESULFONYLAMIDE HYDROCHLORIDE AND OTHER DERIVATIVES OF 2-HYDROXY-1,3-DIAMINES

(75) Inventors: Aslam A. Malik, Cameron Park, CA (US); Hasan Palandoken, Woodland, CA (US); Joy A. Stringer, Carmichael, CA (US); Roland P. Carlson, Folsom, CA (US); John Leach, Gold River, CA (US); Thomas G. Archibald, Fair Oaks, CA (US); Robert G. Miotke, Gold River, CA (US)

(73) Assignee: Aerojet Fine Chemicals LLC, Sacramento, CA (US)

( * ) Notice: Subject to any disclaimer, the term of this patent is extended or adjusted under 35 U.S.C. 154(b) by 0 days.

(21) Appl. No.: 09/747,372

(22) Filed: Dec. 22, 2000

(65) Prior Publication Data

US 2001/0051725 A1 Dec. 13, 2001

Related U.S. Application Data

(60) Provisional application No. 60/172,043, filed on Dec. 23, 1999.

(51) Int. Cl.[7] .................. C07C 209/08; C07C 271/20
(52) U.S. Cl. .......................... 564/483; 560/29
(58) Field of Search ............... 564/483; 560/29

(56) References Cited

U.S. PATENT DOCUMENTS

| 4,760,189 A | 7/1988 | Mercier et al. |
| 5,585,397 A | 12/1996 | Tung et al. |
| 5,723,490 A | 3/1998 | Tung |
| 5,783,701 A | 7/1998 | Tung et al. |
| 5,874,623 A | * 2/1999 | Adkins et al. ............ 564/474 |

FOREIGN PATENT DOCUMENTS

WO    WO 94/05639    3/1994

OTHER PUBLICATIONS

Parkes, et al., *J. Org. Chem.*, 59:3656 (1994).

* cited by examiner

*Primary Examiner*—Peter O'Sullivan
(74) *Attorney, Agent, or Firm*—Townsend & Townsend & Crew LLP

(57) ABSTRACT

The present invention provides a new process for the preparation of 2S,3S-N-isobutyl-N-(2-hydroxy-3-amino-4-phenylbutyl)-p-nitrobenzenesulfonylamide hydrochloride, wherein this compound is prepared directly from the chloromethylalcohol. Importantly, the process of the present invention results in higher yields of 2S,3S-N-isobutyl-N-(2-hydroxy-3-amino-4-phenylbutyl)-p-nitrobenzenesulfonylamide hydrochloride without sacrificing its purity. The processes of the present inventin can be used to prepare not only the 2S,3S-derivative, but also the 2R,3S-, 2S,2R- and the 2R,3R-derivatives.

19 Claims, 1 Drawing Sheet

PREPARATION OF 2S,3S-N-ISOBUTYL-N-(2-HYDROXY-3-AMINO-4-PHENYLBUTYL)-P-NITROBENZENESULFONYLAMIDE HYDROCHLORIDE AND OTHER DERIVATIVES OF 2-HYDROXY-1,3-DIAMINES

This application claims the benefit of provisional application serial No. 60/172,043, filed Dec. 23, 1999.

CROSS-REFERENCE TO RELATED APPLICATION

This patent application claims the benefit of U.S. Provisional Patent Application No. 60/172,043, filed Dec. 23, 1999, which is incorporated herein by reference in its entirety for all purposes.

BACKGROUND OF THE INVENTION

Human immunodeficiency virus (HIV), the causative agent of acquired immunodeficiency syndrome (AIDS), encodes three enzymes, including the well-characterized proteinase belonging to the aspartic proteinase family, the HIV protease. Inhibition of this enzyme has been regarded as a promising approach for treating AIDS. Hydroxyethylamine isosteres have been extensively utilized in the synthesis of potent and selective HIV protease inhibitors. However, this modem generation of HIV protease inhibitors has created an interesting challenge for the synthetic organic chemist. Advanced x-ray structural analysis has allowed for the design of molecules that fit closely into active sites on enzymes creating very effective drug molecules. Unfortunately, these molecules, designed by molecular shape, are often difficult to produce using conventional chemistry.

The modern generation of HIV inhibitors has structural similarities in a central three-carbon piece containing two chiral carbons that link two larger groups on each side (see, e.g., Parkes, et al., *J. Org. Chem.*, 59:3656 (1994)). In general, the chemical bond from the central part to one of the larger groups is a carbon-nitrogen bond which is usually accomplished by reacting an epoxide with an amine. 2S,3S-N-isobutyl-N-(2-hydroxy-3-amino-4-phenylbutyl)-p-nitrobenzenesulfonylamide hydrochloride is a key intermediate in the synthesis of protease inhibitors (see, e.g., U.S. Pat. Nos. 5,585,397, 5,723,490 and 5,783,701 as well as PCT International Publication No. WO 94/05639, the teachings of all of which are incorporated herein by reference). The process currently used to prepare 2S,3S-N-isobutyl-N-(2-hydroxy-3-amino-4-phenylbutyl)-p-nitrobenzenesulfonylamide hydrochloride is illustrated in Figure I.

As illustrated in Figure I, 2S,3S-N-isobutyl-N-(2-hydroxy-3-amino-4-phenylbutyl)-p-nitrobenzenesulfonylamide hydrochloride is prepared by a 4-step process starting from a commercially available (Aerojet Fine Chemicals (Sacramento, Calif.)) starting material, 2S,3S-chloromethylalcohol (2S,3S-CMA). In the first step, 2S,3S-CMA is reacted with sodium hydroxide in THF/ethanol to give the corresponding epoxide in 91% yield. In the second step, the epoxide is dissolved in toluene and reacted with excess isobutylamine at a temperature of about 75° C. to about 80° C. to give Compound I. Reaction of Compound I with p-nitrobenzenesulfonyl chloride (i.e., nosyl chloride) in toluene at a temperature of about 85° C. to about 90° C., followed by deprotecting of the Boc protecting group with aqueous HCl at a temperature of about 85° C. to about 90° C. gives Compound III, i.e., 2S,3S-N-isobutyl-N-(2-hydroxy-3-amino-4-phenylbutyl)-p-nitrobenzenesulfonylamide hydrochloride, in 64% overall yield.

Unfortunately, this process has a number of drawbacks. Some of the drawbacks associated with this process include high reaction temperatures which lead to the formation of side products; low solubility of intermediates in the reaction solvent which requires high processing temperatures during work-up which, in turn, leads to longer cycle times, material handling losses, etc.; and the like. As such, there remains a need in the art for an improved process for preparing 2S,3 S-N-isobutyl-N-(2-hydroxy-3-amino-4-phenylbutyl)-p-nitrobenzenesulfonylamide hydrochloride which overcomes the drawbacks associated with the currently used process. Quite surprisingly, the present invention fulfills this and other needs.

SUMMARY OF THE INVENTION

The present invention provides a new process for the preparation of 2S,3S-N-isobutyl-N-(2-hydroxy-3-amino-4-phenylbutyl)-p-nitrobenzenesulfonylamide hydrochloride, i.e., Compound III. In this new process, one of the chemical steps (i.e., the epoxide step) as well as material handling losses associated with the previously used process have been eliminated. More particularly, using the process of the present invention, the halomethylalcohol, i.e., HMA, (e.g., chloromethylalcohol) is successfully converted to Compound III directly without the need to isolate the Boc-epoxide. Numerous publications have described the synthesis of Compound I-like materials, but they all involve reaction of an epoxide with an amine. As such, the process of the present invention is the first example of a process wherein a protease inhibitor intermediate is prepared directly from the halomethylalcohol. Moreover, the process of the present invention results in a higher yield of Compound III, while not sacrificing its purity. In addition, the process of the present invention allows for the use of the lower purity HMA, thereby eliminating a purification step. Finally, it is pointed out that elimination of the epoxide step eliminates the need to isolate a toxic intermediate (i.e., a mutagen) and, thus, circumvents safety issues involved with dust explosivity of the Boc-epoxide.

Other features, objects and advantages of the invention and its preferred embodiments will become apparent from the detailed description which follows.

DESCRIPTION OF THE INVENTION AND PREFERRED EMBODIMENTS

Figure 1:
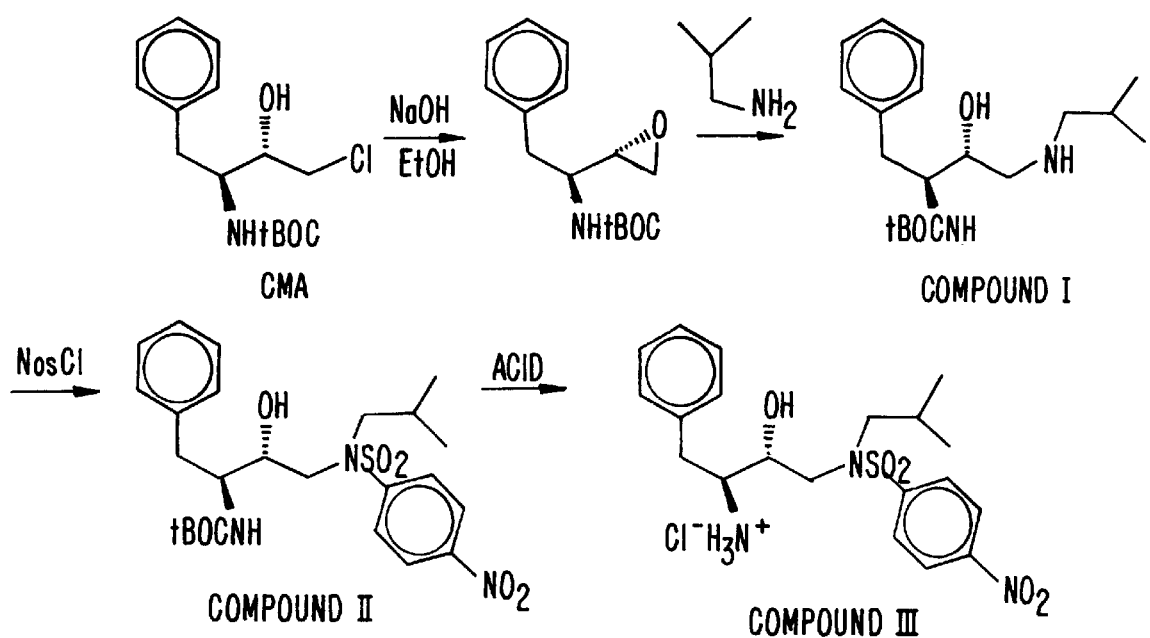
FIG. 1 illustrates the process previously used to prepare 2S,3S-N-isobutyl-N-(2-hydroxy-3-amino-4-phenylbutyl)-p-nitrobenzenesulfonylamide hydrochloride.

It has now been discovered that a protease inhibitor intermediate, i.e., 2S,3S-N-isobutyl-N-(2-hydroxy-3-amino-4-phenylbutyl)-p-nitrobenzenesulfonylamide hydrochloride, can be prepared directly from a halomethylalcohol (HMA) (e.g., chloromethylalcohol) without having to isolate the Boc-epoxide. As such, the present invention provides a new process for the preparation of 2S,3S-N-isobutyl-N-(2-hydroxy-3-amino-4-phenylbutyl)-p-nitrobenzenesulfonylamide hydrochloride, i.e., Compound III, wherein this compound is prepared directly from a HMA. Importantly, the process of the present invention results in higher yields of Compound III, while not sacrificing its purity. Moreover, the process of the present invention can be used to prepare not only the 2S,3S-derivative, but also the 2R,3S-, 2S,2R- and the 2R,3R-derivatives.

As such, the first step in the process for preparing a Compound of Formula III involves the preparation of a compound having the following general formula:

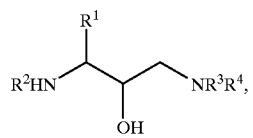

I the process comprising: combining a halomethylalcohol, e.g., chloromethylalcohol, with an amine, e.g., isobutylamine (IBA), to form a reaction mixture, and heating the reaction mixture until the reaction is complete, thereby forming the compound of Formula I, wherein the HMA has the following general formula:

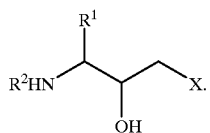

In the above process, X is a leaving group (e.g., a halo group, such as chloro, bromo, fluoro or iodo, a tosylate group, a mesylate group, etc.); $R^1$ is an amino acid side chain or a functionalized amino acid side chain (e.g., an alkyl group, a benzyl group, a phenyl thiomethyl group, a protected hydroxymethyl group, an S-alkyl group, a nitrobenzenyl group, etc.); $R^2$ is a protecting group (e.g., t-Boc (tert-butyloxycarboxy), i-Boc (iso-butyloxycarboxy), Cbz (benzyloxycarboxy), MOC (methoxycarboxy), Fmoc (fluorenylmethoxycarbonyl), dibenzyl, etc.); and $R^3$ and $R^4$ are independently selected and are functional groups including, but not limited to, hydrogen, alkyl, cycloalkyl, aryl and —NHP, wherein P is selected from the group consisting of H, alkyl, cycloalkyl, aryl and a protecting group or, alternatively, $R^3$ and $R^4$ together can form a cyclic structure including, but not limited to, quinoline and isoquinoline, etc.

In a preferred embodiment, the HMA is a 2S,3S-halomethylalcohol (2S,3S-HMA). In a presently preferred embodiment, the 2S,3S-HMA has the following formula:

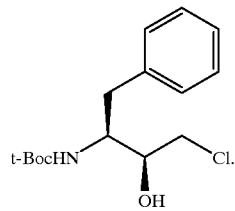

In another preferred embodiment, the Compound of Formula I has the following formula:

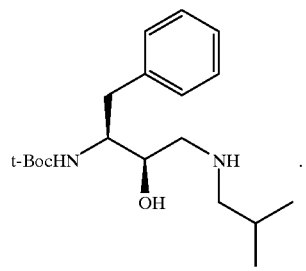

In the above process, a HMA is reacted with an amine at a temperature ranging from about 50° C. to 100° C. to give the compound of Formula I in high yields. In a presently preferred embodiment, the HMA is reacted with an amine at a temperature ranging from about 60° C. to about 75° C. to give the Compound of Formula I in very high yields (about 98–99% yield). The amine used in the above process can be a primary amine, a secondary amine, a substituted amine (e.g., N-substituted sulfonamides, etc.), hydrazines and substituted hydrazines (e.g., N-substituted hydrazine, etc.). Exemplar amines include, but are not limited to, methylamine, ethylamine, isopropylamine, n-butylamine, isobutylamine, cyclohexylamine, benzylamine, para-nitrobenzylamine, dimethylamine, isobutylmethylamine, decahyroquinoline, decahydroisoquinoline, pyrimidine, isobutylparanitrobenzenesulfonamide, methylparanitrobenzenesulfonamide, isobutylmetanitrobenzenesulfonamide, hydrazine, substituted hydrazines, etc.

In a presently preferred embodiment, the amine employed in the above process is isobutylamine (IBA). Importantly, the solvent employed in the previously used method (i.e., toluene) has been eliminated and, in this embodiment, the reaction is conducted in neat IBA, using IBA as the reaction solvent. This simplifies the IBA recovery process (no fractional distillation/column needed to separate IBA from toluene), and allows for the reaction to be carried out at slightly lower temperatures. It has been found, however, that under theses conditions, the reaction times can be relatively long (~30 h). To reduce reaction times, it has been discovered that an acid scavenger can be added to the reaction mixture.

As such, in one embodiment of the above process, an acid scavenger is added to the reaction mixture to reduce reaction times. In a preferred embodiment, the acid scavenger has the general formula: $M^+B^-$, wherein $M^+$ is selected from the group consisting of $K^+$, $Na^+$, $Li^+$, $Ca^{+2}$, $Mg^{+2}$ and $Al^{+2}$; and $B^-$ is selected from the group consisting of $^-OH$, $HCO_3^-$ and $CO_3^{-2}$. In a preferred embodiment, the acid scavenger is sodium bicarbonate. In another preferred embodiment, the acid scavenger is potassium bicarbonate. When an acid scavenger is added to the reaction mixture, about 0.5 to 2 equivalents are added. In a presently preferred embodiment, about 1 equivalent of the acid scavenger is added to the reaction mixture. It has been found that by adding even only 1.05 equivalents of an acid scavenger (e.g., sodium bicarbonate) to the reaction mixture, the reaction times can be reduced from 30 hours to less than 4 hours. Moreover, this reduction in reaction times can be achieved without sacrificing product quality and/or yield. It will be readily apparent to those of skill in the art that other acid scavengers, base phosphates, etc. can be used in the methods of the present invention to reduce reaction times.

Thus, as illustrated in Table I, the reaction rates of the base catalyzed reaction of chloromethylalcohol (CMA) with isobutylamine are comparable to those of the epoxide with isobutylamine, with the reaction being substantially complete in 3 hours.

TABLE I

| Rxn Time (h) | % Compound I |
|---|---|
| 0 | 0.15 |
| 1 | 90.8 |
| 2 | 97.7 |
| 3 | 98.6 |
| 4 | 98.8 |

Moreover, it is pointed out that the Boc-epoxide employed in the previously used method is thermally unstable, and at higher temperatures (>70° C.) will undergo a deprotecting reaction to give free amine which, in turn, leads to a variety of side-reactions. In contrast, HMA, e.g., CMA, is more thermally stable than Boc-epoxide. The higher thermal stability of HMA, e.g., CMA, coupled with lower reaction/processing temperatures allows for Compound III to be prepared in a much higher yield and purity. Moreover, using the above process, the purity of isolated Compound I is in the neighborhood of 98.7 to 98.8% (area %) by HPLC. Typical results for the reaction of 2S,3S-CMA with isobutylamine to give Compound I are illustrated below:

TABLE II

| Reaction # | Scale* | Yield | Purity |
|---|---|---|---|
| CPO86-135 (HP) | 100 g | 98.5% | 98.8% |
| CPO86-143 (HP) | 100 g | 98.5% | 98.7% |
| CPO86-147 (HP) | 100 g | ND | 98.8% |
| CPO86-160 (HP) | 250 g | 99% | 98.8% |

In one embodiment, the above process further comprises recovering (e.g., isolating and purifying) the Compound of Formula I from the reaction mixture. However, in a presently preferred embodiment, the Compound of Formula I is filtered and used in the next step without first being purified.

The second step in the process for preparing a Compound of Formula III involves the preparation of a compound having the following general formula:

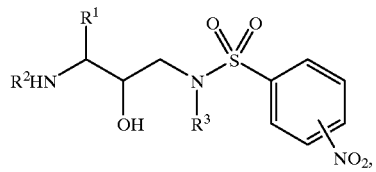

II the process comprising: (a) combining p-nitrobenzenesulfonyl chloride, i.e., nosyl chloride, with an alkyl acetate to form a first reaction mixture; (b) combining a tertiary amine (e.g., triethylamine (TEA)) with a compound of Formula I in an aromatic solvent (e.g., toluene) to form a second reaction mixture, the compound of Formula I having the following general formula:

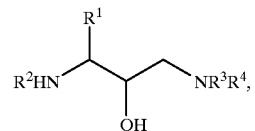

I and, (c) adding the first reaction mixture with the second reaction mixture to form a third reaction mixture, and heating the third reaction mixture until the reaction is complete, thereby forming the compound of Formula II.

In the above process, $R^1$ is an amino acid side chain or a functionalized amino acid side chain; $R^2$ is a protecting group; and $R^3$ and $R^4$ are independently selected and are functional groups including, but not limited to, hydrogen, alkyl, cycloalkyl, aryl and —NHP, wherein P is selected from the group consisting of H, alkyl, cycloalkyl, aryl and a protecting group or, alternatively, $R^3$ and $R^4$ together can form a cyclic structure including, but not limited to, quinoline and isoquinoline. In a presently preferred embodiment, the compound of Formula I has the following general formula:

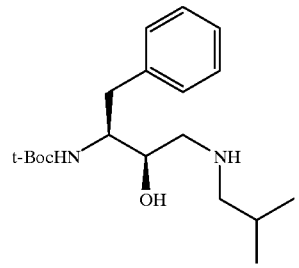

In another preferred embodiment, the Compound of Formula II has the following general formula:

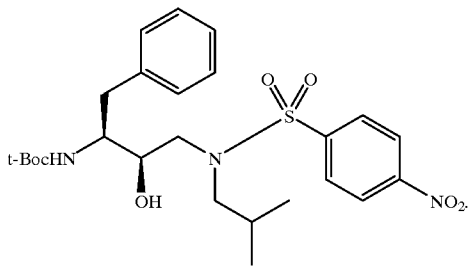

In the first step of the above process, nosyl chloride is combined with an alkyl acetate to form a first reaction mixture. Alkyl acetates suitable for use include, but are not limited to, methyl acetate, ethyl acetate, isopropyl acetate, isobutyl acetate, etc. In a presently preferred embodiment, ethyl acetate is employed. In the second step of the above process, a tertiary amine is combined with a Compound of Formula I in an aromatic solvent to form a second reaction mixture. Exemplar tertiary amines include, but are not limited to, triethylamine, diisopropylethylamine, pyridine and N-methylmorpholine. In a presently preferred embodiment, triethylamine is used. Suitable aromatic solvents, include, but are not limited to, toluene, benzene and xylene. In a presently preferred embodiment, toluene is used. In the third step of the above process, the first reaction mixture is added to the second reaction mixture to form a third reaction mixture, and the third reaction mixture is heated until the reaction is complete. In a presently preferred embodiment, the first reaction mixture is heated or warmed prior to adding it to the second reaction mixture. The third reaction mixture is heated to a temperature ranging from about 50° C. to about 100° C. and, more preferably, to a temperature ranging from about 60° C. to about 75° C.

Ethyl acetate is a good solvent for Compound I and Compound II intermediates; however, under certain conditions, Compound I will react with ethyl acetate to give N-acetyl Compound I. As such, it has now been surprisingly discovered that the best way to carry out the above process, i.e., the second step in the preparation of the Compound of Formula III, is to dissolve the nosyl chloride in ethyl acetate (nosyl chloride is not very soluble in toluene), and then add it to a solution of the Compound of Formula I in toluene that has been warmed to a temperature of about 70° C. Under these conditions, the reaction is instantaneous and is complete when the addition is done. Moreover, since nosyl chloride is much more reactive than ethyl acetate, formation of the N-acetyl Compound I is not detected. Further, addition of ethyl acetate to the reaction mixture improves the solubility of Compound II in the reaction mixture, thereby allowing the processing to be conducted at about 70° C. instead of at about 85° C. Use of ethyl acetate as a co-solvent also improves the partitioning of the Compound of Formula II into the organic phase and, thus, minimizes loss due to product loss in aqueous phase. Further, use of lower reaction temperature (70° C. versus 85–90° C.) also improves the quality of the Compound of Formula II since side reactions, such as de-protecting, etc., are minimized at lower temperatures.

In an alternative embodiment, the Compound of Formula II can be prepared directly from a HMA. As such, the present invention provides a process for the preparation of a compound having the general formula:

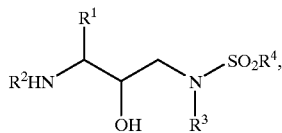

II the process comprising: combining a halomethyl alcohol (HMA) with a sulfonamide to form a reaction mixture, and heating said reaction mixture until the reaction is complete, thereby forming the compound of Formula II, wherein said HMA has the following general formula:

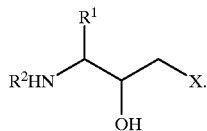

In the above process, $R^1$ is an amino acid side chain or a functionalized amino acid side chain; $R^2$ is a protecting group; $R^3$ is a functional group including, but not limited to, hydrogen, alkyl, cycloalkyl, aryl and —NHP, wherein P is selected from the group consisting of H, alkyl, cycloalkyl, aryl and a protecting group; $R^4$ is a functional group including, but not limited to, alkyl, cycloalkyl and aryl; and X is a leaving group.

In a preferred embodiment, the HMA is a 2S,3S-halomethyl-alcohol (2S,3S-HMA). In a presently preferred embodiment, the 2S,3S-HMA has the following formula:

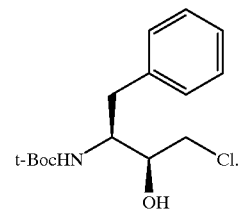

In the above process, the HMA is reacted with a sulfonamide. Suitable sulfonamides include those having the following general formula:

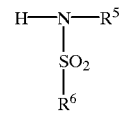

wherein: $R^5$ and $R^6$ are independently selected and are functional groups including, but not limited to, alkyl, cycloalkyl and aryl. In a preferred embodiment, $R^5$ is alkyl and $R^6$ is aryl. In a further preferred embodiment, the aryl has the general formula:

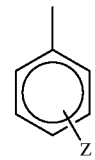

wherein: Z is a functional group including, but not limited to, hydrogen, alkyl, halogen, hydroxy, alkoxy, —NO$_2$ and —NAP, wherein P is a protecting group. In a preferred embodiment, the sulfonamide is selected from the group consisting of isobutylparanitrobenzenesulfonamide, isobutylmetanitrobenzenesulfonamide and isobutylorthonitrobenzenesulfonamide.

In one embodiment of the above process, an acid scavenger can be added to the reaction mixture to reduce reaction times. In a preferred embodiment, the acid scavenger has the general formula: $M^+B^-$, wherein $M^+$ is selected from the group consisting of $K^+$, $Na^+$, $Li^+$, $Ca^{+2}$, $Mg^{+2}$ and $Al^{+2}$; and $B^-$ is selected from the group consisting of $^-OH$, $HCO_3^-$ and $CO_3^{-2}$. In a preferred embodiment, the acid scavenger is sodium bicarbonate. In another preferred embodiment, the acid scavenger is potassium bicarbonate. When an acid scavenger is added to the reaction mixture, about 0.5 to 2 equivalents are added. In a presently preferred embodiment, about 1 equivalent of the acid scavenger is added to the reaction mixture. In this process, a HMA is reacted with a sulfonamide at a temperature ranging from about 50° C. to 125° C. to give the compound of Formula II in high yields. In a presently preferred embodiment, the HMA is reacted with a sulfonamide at a temperature ranging from about 60° C. to about 80° C. to give the Compound of Formula II in very high yields.

The final step in the process of the present invention involves the conversion of a Compound of Formula II to a Compound of Formula III, the Compound of Formula III having the following general formula:

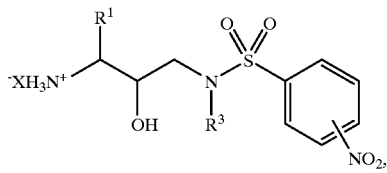

in which $R^1$ is an amino acid side chain or a functionalized amino acid side chain; $R^3$ is a functional group including, but not limited to hydrogen, alkyl, cycloalkyl, aryl and —NHP, wherein P is selected from the group consisting of H, alkyl, cycloalkyl, aryl and a protecting group; and $X^-$ is the conjugate base of an acid having a $pK_a$ of less than about 4. The process for converting a Compound of Formula II to a Compound of Formula III comprises: (a) combining a Compound of Formula II with an aromatic solvent/alkyl acetate (e.g., toluene/ethyl acetate) to form a reaction mixture, and heating the reaction mixture, the Compound of Formula II having the following general formula:

II

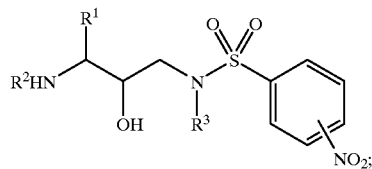

and, (b) treating the reaction mixture with an acid having a $pK_a$ of less than about 4 (e.g., hydrochloric acid (HCl)) until the reaction is complete, thereby forming the Compound of Formula III. In a presently preferred embodiment, this process further comprises recovering the Compound of Formula III from the reaction mixture by cooling to 5° C. and filtering.

In the above process, $R^1$ is an amino acid side chain or a functionalized amino acid side chain; $R^2$ is a protecting group; and $R^3$ is a member selected from the group consisting of hydrogen, alkyl, cycloalkyl, aryl and —NHP, wherein P is selected from the group consisting of H, alkyl, cycloalkyl, aryl and a protecting group; and $X^-$ is the conjugate base of said acid.

In a presently preferred embodiment the Compound of Formula II has the following formula:

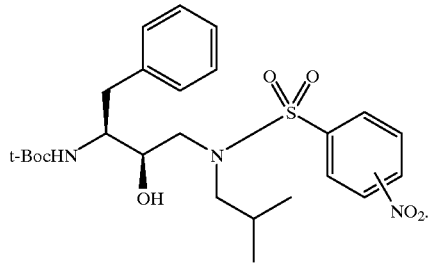

In another preferred embodiment, the Compound of Formula III has the following general formula:

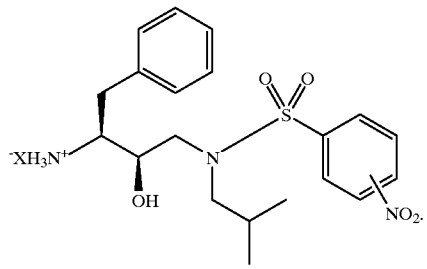

In step (b) of the above process, the reaction mixture is treated or contacted with an acid having a $pK_a$ of less than about 4. Suitable acids include, but are not limited to, HCl, HBr, $CF_3CO_2H$, $CF_3SO_3H$, $CH_3SO_3H$, $H_2SO_4$, citric acid, tartaric acid, oxalic acid and p-toluene sulfonic acid. The reaction mixture is treated with the acid for a time period of at lease about 0.5 hours and, typically, for a period of time ranging from about 1 to about 5 hours. In a presently preferred embodiment, the acid is aqueous hydrochloric acid (HCl). In this embodiment, the hydrochloric acid can be, for example, about 37% aqueous hydrochloric acid. In another preferred embodiment, the hydrochloric acid is gaseous hydrochloric acid. In this embodiment, the gaseous hydrochloric acid can be bubbled through the reaction mixture. In another presently preferred embodiment, the acid is methanesulfonic acid ($CH_3SO_3H$). In a presently preferred embodiment, the Compound of Formula III is recovered from the reaction mixture.

In addition to the foregoing, it has also been discovered that a halogenated solvent (e.g., methylene chloride) is a superior solvent than toluene or toluene/ethyl acetate for synthesizing the Compounds of Formulae II and III. The higher solubility of Compound I–III intermediates in a halogenated solvent (e.g., methylene chloride) allows for the reactions to be carried out at much lower temperatures (about 30 to 35° C. lower than the toluene/ethyl acetate process and about 45–50° C. lower than the toluene process). The ability to conduct the reactions at lower temperatures has a profound effect on the quality and yield of the resulting material. Low reaction temperatures minimize decomposition and other side-reactions (e.g., deprotecting), thereby leading to products with fewer impurities which, in turn, leads to improved quality and higher yield (15 to 20% higher yield). It has been found that the rate of the deprotecting reaction with, for example, aqueous HCl is much slower in a halogenated solvent (e.g., methylene chloride) than in toluene or toluene/ethyl acetate. For example, in toluene/ethyl acetate the time required to achieve >99% conversion is about 3 hours, whereas in methylene chloride, it is nearly 5 days. However, it has surprisingly been discovered that the use of, for example, gaseous HCl, instead of aqueous HCl, will reduce the reaction time from 5 days to 3 hours. An additional advantage for using gaseous HCl is that it does not require additional stripping to remove the water. When HCl is employed as the acid, the final product (Compound III) is a hydrochloride salt, and it is important to remove water in order to achieve a good yield. However, this problem is eliminated when anhydrous gaseous HCl is used. Moreover, the product quality of crude Compound III prepared by the halogenated solvent route is much better than that of crude Compound III prepared by the toluene or toluene/ethyl acetate processes. Consequently, the yield of the isolated Compound III is nearly 15% higher with the halogenated solvent process. In addition, the intermediates do not have to be isolated when a halogenated solvent (e.g., methylene chloride) is used. It is noted that, e.g., the sulfonamide impurity is soluble in methylene chloride; otherwise, it is very difficult to remove.

As such, in one embodiment, the present invention provides a process for preparing a compound having the following general formula:

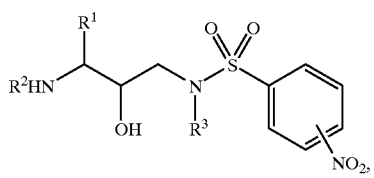

II the process comprising: (a) combining nosyl chloride with a halogenated solvent (e.g., methylene chloride) to form a first reaction mixture; (b) combining a tertiary amine (e.g., triethylamine) with a compound of Formula I in a halogenated solvent (e.g., methylene chloride) to form a second reaction mixture, the compound of Formula I having the following general formula:

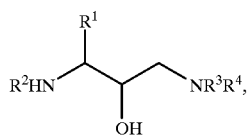

I and, (c) adding the first reaction mixture to the second reaction mixture to form a third reaction mixture, and heating the third reaction mixture to a temperature ranging from about 10° C. to about 50° C. and, more preferably, to a temperature ranging from about 30° C. to about 35° C. until the reaction is complete, thereby forming the compound of Formula II. In a presently preferred embodiment, the first reaction mixture is heated or warmed prior to adding it to the second reaction mixture.

In the above process, $R^1$ is an amino acid side chain or a functionalized amino acid side chain; $R^2$ is a protecting group; and $R^3$ is a functional group including, but not limited to, hydrogen, alkyl, cycloalkyl, aryl and —NHP, wherein P is selected from the group consisting of H, alkyl, cycloalkyl, aryl and a protecting group.

In a presently preferred embodiment, the Compound of Formula I has the following formula:

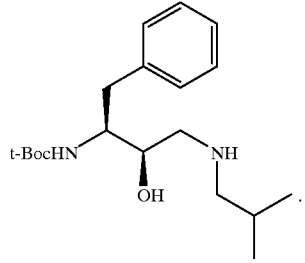

In another preferred embodiment, the Compound of Formula II has the following formula:

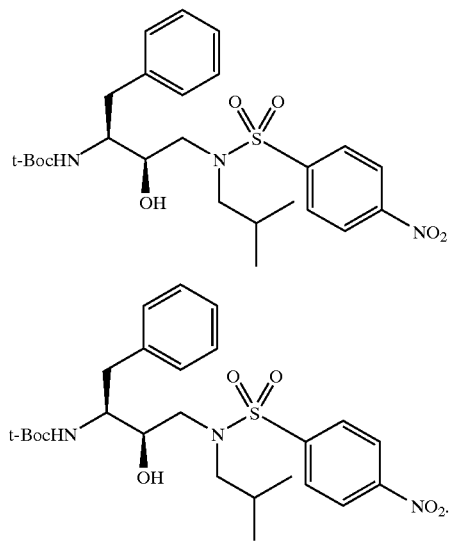

In the above process, a halogenated solvent is employed. Suitable halogenated solvents include, but are not limited to, methylene chloride, chloroform, trifluorotoluene (oxsol), parachlorotrifluorotoluene and trichloroethylene. In a preferred embodiment, the halogenated solvent is methylene chloride. Suitable tertiary amines include, but are not limited to, triethylamine, diisopropylethylamine, pyridine and N-methylmorpholine. In a preferred embodiment, the tertiary amine is triethylamine.

In another embodiment, the present invention provides a process for preparing a compound having the following general formula:

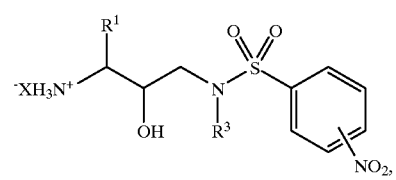

III the process comprising: (a) combining a compound of Formula II with a halogenated solvent (e.g., methylene chloride) to form a reaction mixture and heating the reaction mixture to a temperature ranging from about 10° C. to about 50° C. and, more preferably, to a temperature ranging from about 30° C. to about 35° C., the compound of Formula II having the following general formula:

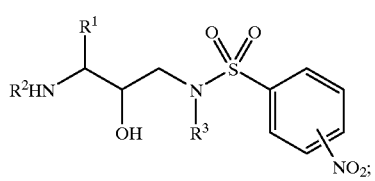

II and, (b) treating the reaction mixture with an acid having a $pK_a$ of less than about 4 (e.g., hydrochloric acid) until the reaction is complete, thereby forming the compound of Formula III. Exemplar halogenated solvents includes, but are not limited to, the following: methylene chloride, chloroform, trifluorotoluene (oxsol), parachlorotrifluorotoluene and trichloroethylene. In a presently preferred embodiment, the halogenated solvent is methylene chloride.

In the above process, $R^1$ is an amino acid side chain or a functionalized amino acid side chain; $R^2$ is a protecting group; and $R^3$ is a member selected from the group consisting of hydrogen, alkyl, cycloalkyl, aryl and —NHP, wherein P is selected from the group consisting of H alkyl, cycloalkyl, aryl and a protecting group; and $X^-$ is the conjugate base of the acid employed in the reaction.

In a presently preferred embodiment, the Compound of Formula II has the following formula:

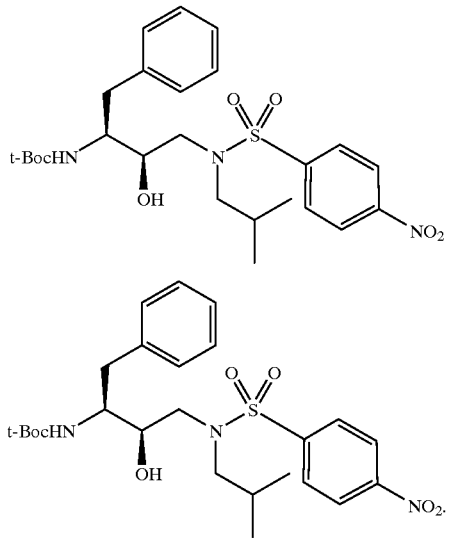

In another preferred embodiment, the Compound of Formula III has the following general formula:

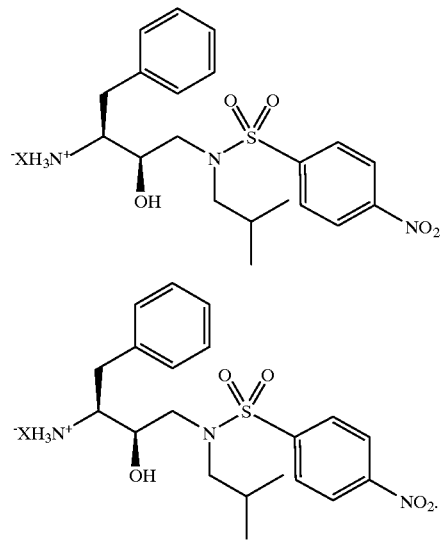

In step (b) of the above process, the reaction mixture is treated or contacted with an acid having a $pK_a$ of less than about 4. Exemplar acids include, but are not limited to, HCl, HBr, $CF_3CO_2H$, $CF_3SO_3H$, $CH_3SO_3H$, $H_2SO_4$, citric acid, tartaric acid, oxalic acid and p-toluene sulfonic acid. The reaction mixture is treated with the acid until the reaction is complete and, typically, for a time period of at lease about 0.5 hours and, more preferably, for a period of time ranging from about 1 to about 5 hours. In one preferred embodiment, the hydrochloric acid is aqueous hydrochloric acid. In this embodiment, the hydrochloric acid can be, for example, about 37% aqueous hydrochloric acid. In another preferred embodiment, the hydrochloric acid is gaseous hydrochloric acid. In this embodiment, the gaseous hydrochloric acid can be bubbled through the reaction mixture. In another preferred embodiment, the acid is methanesulfonic acid ($CH_3SO_3H$). In a presently preferred embodiment, the Compound of Formula III is recovered from the reaction mixture.

In another embodiment, the present invention provides a process for preparing a Compound of Formula III from a HMA, the Compound of Formula III having the following general formula:

III

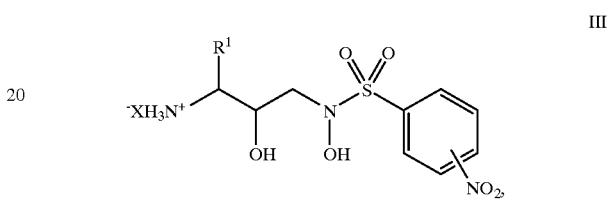

the process comprising: (a) combining a halomethyl alcohol (HMA) and an amine (e.g., isobutylamine (IBA)) in a halogenated solvent (e.g., methylene chloride) with an acid scavenger to form a reaction mixture, and heating the reaction mixture to a temperature ranging from about 10° C. to about 50° C. and, more preferably, to a temperature ranging from about 30° C. to about 35° C., wherein the HMA has the following general formula:

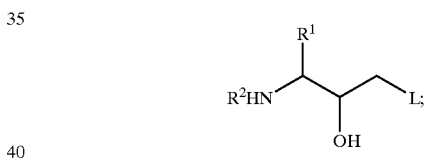

(b) adding to the first reaction mixture nosyl chloride while stirring the reaction mixture, and recovering the organic layer of the reaction mixture to form a solution; and (c) reacting the solution with an acid having a $pK_a$ of less than about 4 until the reaction is complete, thereby forming the compound of Formula III.

In the above process, $R^1$ is an amino acid side chain or a functionalized amino acid side chain; $R^2$ is a protecting group; $R^3$ is a functional group including, but not limited to, hydrogen, alkyl, cycloalkyl, aryl and —NHP, wherein P is selected from the group consisting of H, alkyl, cycloalkyl, aryl and a protecting group; and L is a leaving group.

In a presently preferred embodiment, the HMA is a 2S,3S-HMA. In a presently preferred embodiment, the 2S,3S-HMA has the following formula:

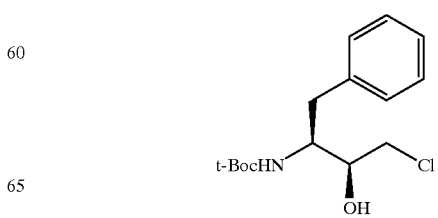

-continued

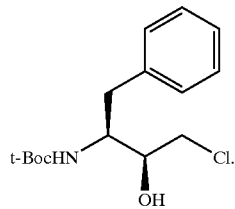

In another presently preferred embodiment, the Compound of Formula III has the following formula:

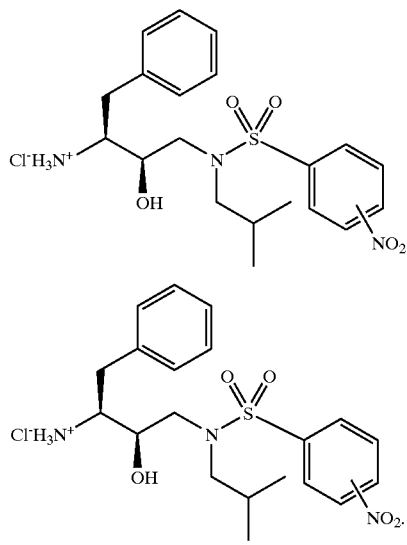

In the above process, an amine is combined with a halogenated solvent. Suitable amines include, but are not limited to, primary amines, secondary amines, substituted amines, hydrazines and substituted hydrazines. Exemplar amines include, but are not limited to, methylamine, ethylamine, isopropylamine, n-butylamine, isobutylamine, cyclohexylamine, benzylamine, paranitrobenzylamine, dimethylamine, isobutylmethylamine, decahyroquinoline, decahydroisoquinoline, pyrimidine, isobutylhydrazine and t-Boc-hydrazine. In a preferred embodiment, the amine is a primary amine. In a presently preferred embodiment, the amine is isobutylamine (IBA), preferably neat IBA. In the above process, a halogenated solvent is employed. Exemplar halogenated solvents includes, but are not limited to, the following: methylene chloride, chloroform, trifluorotoluene (oxsol), parachlorotrifluorotoluene and trichloroethylene. In a presently preferred embodiment, the halogenated solvent is methylene chloride.

In step (c) of the above process, the solution from step (b) is treated or contacted with an acid having a $pK_a$ of less than about 4. Exemplar acids include, but are not limited to, HCl, HBr, $CF_3CO_2H$, $CF_3SO_3H$, $CH_3SO_3H$, $H_2SO_4$, citric acid, tartaric acid, oxalic acid and p-toluene sulfonic acid. The solution is treated with the acid until the reaction is complete. Typically, the solution is treated for a time period of at lease about 0.5 hours and, more preferably, for a time period ranging from about 1 to about 5 hours. In one preferred embodiment, the acid is hydrochloric acid. In another preferred embodiment, the acid is methanesulfonic acid ($CH_3SO_3H$).

In yet another embodiment, the present invention provides a process for preparing a Compound of Formula III from a compound of Formula I, the Compound of Formula III having the following general formula:

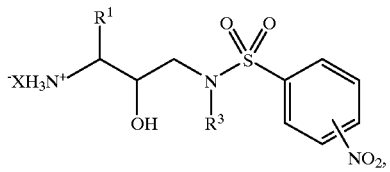

III the process comprising: (a) adding a Compound of Formula I in a halogenated solvent (e.g., methylene chloride) with a tertiary amine and nosyl chloride to form a reaction mixture, and heating the reaction mixture at a temperature ranging from about 10° C. to about 50° C. and, more preferably, to a temperature ranging from about 30° C. to about 35° C.; the compound of Formula I having the following general formula:

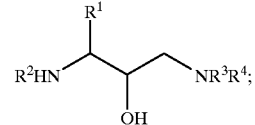

and (b) reacting the reaction mixture with an acid having a $pK_a$ of less than about 4 until the reaction is complete, thereby forming the Compound of Formula III.

In the above process, $R^1$ is an amino acid side chain or a functionalized amino acid side chain; $R^2$ is a protecting group; and $R^3$ is a member selected from the group consisting of hydrogen, alkyl, cycloalkyl, aryl and —NHP, wherein P is selected from the group consisting of H alkyl, cycloalkyl, aryl and a protecting group; and $X^-$ is the conjugate base of the acid used in step (b).

In a presently preferred embodiment, the Compound of Formula I has the following formula:

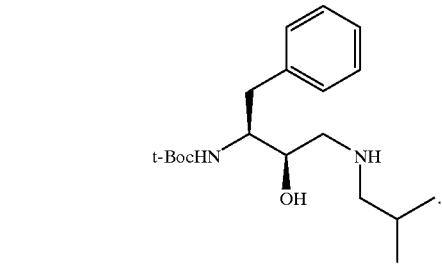

In another preferred embodiment, the Compound of Formula III has the following formula:

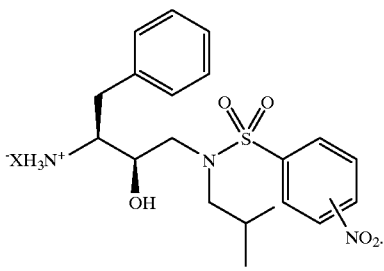

In the above process, a tertiary amine is combined with a halogenated solvent. Suitable tertiary amines include, but are not limited to, triethylamine, diisopropylethylamine, pyridine and N-methylmorpholine. In a presently preferred embodiment, triethylamine is used. Exemplar halogenated solvents includes, but are not limited to, the following: methylene chloride, chloroform, trifluorotoluene (oxsol), parachlorotrifluorotoluene and trichloroethylene. In a presently preferred embodiment, the halogenated solvent is methylene chloride.

In step (b) of the above process, the reaction mixture is reacted with an acid having a $pK_a$ of less than about 4. Exemplar acids include, but are not limited to, HCl, HBr, $CF_3CO_2H$, $CF_3SO_3H$, $CH_3SO_3H$, $H_2SO_4$, citric acid, tartaric acid, oxalic acid and p-toluene sulfonic acid. The solution is treated with the acid until the reaction is complete. Typically, the solution is treated for a time period of at least about 0.5 hours and, more preferably, for a time period ranging from about 1 to about 5 hours. In one preferred embodiment, the acid is hydrochloric acid. In another preferred embodiment, the acid is methanesulfonic acid ($CH_3SO_3H$).

In a presently preferred embodiment, the process further comprises washing 20 the reaction mixture; heating the reaction mixture to a temperature ranging from about 40° C. to about 45° C.; and then azeotropically drying the reaction mixture prior to step (b). In another preferred embodiment, the Compound of Formula III is recovered from the reaction mixture. In one such embodiment, the recovery step comprises: (i) cooling the reaction mixture to a temperature of about −5° C.; (ii) filtering the reaction mixture to remove the N-isobutyl-p-nitrobenzenesulfonamide impurities and provide the compound of Formula III; and (iii) washing the compound of Formula III and then drying it in vacuo.

Using the above processes, 2S,3S-N-isobutyl-N-(2-hydroxy-3-amino-4-phenylbutyl)-p-nitrobenzenesulfonylamide hydrochloride can be prepared directly from the chloromethylalcohol (CMA) without having to isolate the Boc-epoxide. The process of the present invention is the first demonstration of a process wherein a protease inhibitor intermediate is prepared directly from the halomethylalcohol. Again, this is extremely helpful because elimination of the epoxide eliminates the need to isolate a toxic intermediate (i.e., a mutagen) and, thus, circumvents safety issues involved with dust explosivity of the Boc-epoxide. Importantly, the process of the present invention results in higher yields of Compound III, while not sacrificing its purity.

Those of skill in the art will readily understand that the term "alkyl," as used herein, refers to a branched or unbranched, saturated or unsaturated, monovalent hydrocarbon radical having from 1–12 carbons and, preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc. As used herein, the term alkyl encompasses "substituted alkyls." Substituted alkyl refers to alkyl as just described including one or more functional groups such as lower alkyl, aryl, aralkyl, acyl, halogen (i.e., alkylhalos, e.g., $CF_3$), hydroxy (e.g., hydroxymethyl), amino, alkylamino, acylamino, acyloxy, alkoxy (e.g., methoxymethyl), mercapto and the like. These groups may be attached to any carbon atom of the lower alkyl moiety.

The term "cycloalkyl," by itself or in combination with other terms, represents cyclic versions of "alkyl." Examples of cycloalkyl include cyclopentyl, cyclohexyl, 1-cyclohexenyl, 3-cyclohexenyl, cycloheptyl, and the like. The cycloalkyl group may be substituted or unsubstituted.

The term "alkoxy" is used herein to refer to the —OR group, where R is a lower alkyl, substituted lower alkyl, aryl, substituted aryl, aralkyl or substituted aralkyl. Suitable alkoxy radicals include, for example, methoxy, ethoxy, phenoxy, t-butoxy (e.g., methoxyethoxy, methoxymethoxy, etc.), etc.

The term "aryl," as used herein, refers to an aromatic substituent which may be a single ring or multiple rings which are fused together, linked covalently, or linked to a common group such as an ethylene or methylene moiety. The aromatic ring(s) may include phenyl, naphthyl, biphenyl, diphenylmethyl, 2,2-diphenyl-1-ethyl, and may contain a heteroatom, such as thienyl, pyridyl and quinoxalyl. The aryl group may also be substituted with halogen atoms, or other groups such as nitro, carboxyl, alkoxy, phenoxy, and the like. Additionally, the aryl group may be attached to other moieties at any position on the aryl radical which would otherwise be occupied by a hydrogen atom (such as 2-pyridyl, 3-pyridyl and 4-pyridyl).

In view of the foregoing, it will be readily apparent to those of skill in the art that the foregoing processes can be used to prepare not only the 2S,3S-derivative, but also the 2R,3S-, 2S,2R- and the 2R,3R-derivatives. Again, the process of the present invention results in higher yields of these derivatives, while not sacrificing their purity.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

EXAMPLES

I. Process A: Toluene/Ethyl Acetate Process:

A. Preparation of Compound I

A mixture of 2S,3S-CMA (251.8 g, 0.84 mol), isobutylamine 737.8 g (10.1 mol) and sodium hydrogen carbonate (77.6 g, 92 mol) in water (323.9 g) is heated at a gentle reflux (~60° C.) for 5 h. Water (1000 g) is added and excess isobutyl amine is removed by distillation under nitrogen at an internal reaction temperature of 70° C. (The recovery is approximately 85% and the recovered IBA can be recycled). Additional water (500 g) is added and the product is isolated by filtration. The precipitated solid is washed with water and dissolved in toluene (1500 g). The solution is reduced in volume by ⅓ by distillation at 70° C. under reduced pressure (300 mm-Hg) to remove water and residual isobutylamine. The solution of Compound I in toluene is used directly in synthesis of Compound II. However, in order to obtain yield/purity data, Compound I is isolated by evaporation of the solvent and the resulting solid is dried in oven to constant weight. The yields normally range in the neighborhood of 98.5 to 99% with purities (HPLC) ranging in the neighborhood of 98.7 to 98.8%. The isolated product was characterized by 1H/13C NMR and by HPLC/TLC analysis.

B. Preparation of Compound II

Solution of Compound I in toluene was warmed to 70° C. and treated with triethylamine (220 g, 2.18 mol). Then, a solution of p-nitrobenzenesulfonyl chloride (195 g, 0.88 mol) in ethyl acetate (1 l) was added over 3 h. The organic mixture was then washed sequentially at 65–70° C. with water (400 mL), 5% aqueous sodium hydrogen carbonate (400 mL) and water (400 mL). The product is obtained as a solution in toluene/ethyl acetate and is used directly in synthesis of Compound III. The yields, as determined by evaporating the solvent and isolating crude Compound II, were in the neighborhood of 97 to 98%.

C. Preparation of Compound III

The solution of Compound II in toluene/ethyl acetate at 65° C.-70° C. was treated with 37% aqueous hydrochloric acid (160 g, 1.64 mol) over a period of 2 h. The mixture was then distilled at 70° C. under reduced pressure (500–600 mm-Hg) until the residual ethyl acetate content was less than 5 mol % in toluene (as determined by $^1$H NMR analysis), and the water content was less than 1% (as determined by Karl Fischer analysis). When distillation was complete, the toluene volume was adjusted to 15% solids and ethanol (360 mL, denatured with 5 wt % Methanol) was added. The mixture was cooled to ambient temperature over 2 h, held at ambient for 1 h, then cooled to −5° C. to −10° C. for 1 h. The precipitated solid was isolated by filtration, washed with toluene and n-hexanes, and dried in vacuo at 80° C. to give 247 g (73%) of Compound III. The purity of Compound III as determined by HPLC was 99.2 wt % (99.8 area%). Compound III was also characterized by 1H/13C NMR analysis.

II. Process B: Methylene Chloride Process

A. One Pot Process

A solution of 2S,3S-CMA (44 g, 0.146 mol), isobutylamine (11 g, 0.150 mol) in 270 mL of methylene chloride was stirred with sodium hydrogen carbonate (33 g, 0.4 mol) in water (100 g) for 5 h. is heated at a gentle reflux (~30° C.) for 6 h. Then nosyl chloride (35.4 g, 0.157 moles) and triethylamine (17.7 g, 0.175 moles) was added and the mixture stirred for 6 h at 30–35° C. The organic layer was removed and the residue washed with water (100 mL). Gaseous HCl was bubbled through the solution for 2–3 hours until the reaction was complete as indicated by HPLC analysis. The residual acid is removed with a stream of nitrogen gas and the reaction mixture was cooled to −5° C. for 1 h. The mixture was filtered to give 60 g (89%) of Compound III with 99.7% purity by HPLC.

B. Process Starting with Compound I

A solution of triethylamine (17.7 g, 0.175 mol) and Compound I (49.0 g 1.46 mol) in methylene chloride (270 mL) was heated to 30–35° C. and nosyl chloride (35.4 g, 0.157 mol) in methylene chloride was added over 3 h. The solution is heated to 35° C. and washed sequentially with water (65 mL), 5% sodium bicarbonate solution (60 mL) and water (80 mL). The solution was heated reflux and water removed azeotropically. When Karl Fischer analysis of the solution indicated that less than 0.1% of water remained, the solution was cooled to ambient. Hydrogen chloride gas was passed through the solution for 3 h until HPLC analysis indicated that the reaction was complete. The mixture was cooled to 0–5° C. and filtered to give a white solid. The solid was washed with hexanes (65 mL) and dried in vacuo to give 59.5 g (89%) of compound III that was 99.7% pure by HPLC analysis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A process for the preparation of a compound having the following general formula:

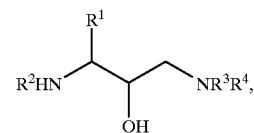

said process comprising: combining a halomethyl alcohol (HMA) with an amine and an acid scavenger to form a reaction mixture, and heating said reaction mixture until the reaction is complete, thereby forming the compound of Formula I; wherein said HMA has the following general formula:

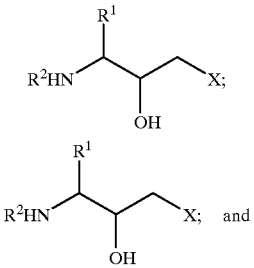

wherein:
  $R^1$ is an amino acid side chain or a functionalized amino acid side chain;
  $R^2$ is a protecting group;
  $R^3$ and $R^4$ are independently selected from the group consisting of hydrogen, alkyl, cycloalkyl, aryl and —NHP, wherein P is selected from the group consisting of H, alkyl, cycloalkyl, aryl and a protecting group, or $R^3$ and $R^4$ together form a cyclic structure selected from the group consisting of quinoline and isoquinoline; and
  X is a leaving group.

2. The process in accordance with claim 1, wherein said HMA is a 2S,3S-HMA.

3. The process in accordance with claim 1, wherein X is a halogen.

4. The process in accordance with claim 3, wherein X is chloro or bromo.

5. The process in accordance with claim 1, wherein $R^1$ is a member selected from the group consisting of an alkyl group, a benzyl group, a phenyl thiomethyl group, a protected hydroxymethyl group, an S-alkyl group and a nitrobenzyl group.

6. The process in accordance with claim 1, wherein $R^2$ is a protecting group selected from the group consisting of t-Boc, i-Boc, Moc, Cbz and Fmoc.

7. The process in accordance with claim 2, wherein said 2S,3S-HMA has the following general formula:

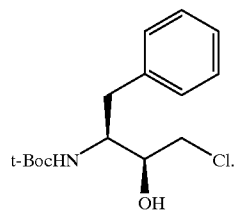

8. The process in accordance with claim 1, wherein said amine is a member selected from the group consisting of primary amines, secondary amines, substituted amines, hydrazines and substituted hydrazines.

9. The process in accordance with claim 1, wherein said amine is a member selected from the group consisting of methylamine, ethylamine, isopropylamine, n-butylamine, isobutylamine, cyclohexylamine, benzylamine, para-nitrobenzylamine, dimethylamine, isobutylmethylamine, decahyroquinoline, decahydroisoquinoline, pyrimidine, isobutylhydrazine and t-Boc-hydrazine.

10. The process in accordance with claim 1, wherein said amine is isobutylamine (IBA).

11. The process in accordance with claim 1, wherein said acid scavenger has the general formula $M^+B^-$, wherein $M^+$ is selected from the group consisting of $K^+$, $Na^+$, $Li^+$, $Ca^{+2}$, $Mg^{+2}$ and $Al^{+2}$; and $B^-$ is selected from the group consisting of $^-OH$, $HCO_3^-$ and $CO_3^{-2}$.

12. The process in accordance with claim 1, wherein said acid scavenger is sodium bicarbonate.

13. The process in accordance with claim 1, wherein said acid scavenger is potassium bicarbonate.

14. The process in accordance with claim 1, wherein about 0.5 to about 2 equivalents of said acid scavenger is present in said reaction mixture.

15. The process in accordance with claim 1, wherein about 1 equivalent of said acid scavenger is present in said reaction mixture.

16. The process in accordance with claim 1, wherein said reaction mixture is heated to a temperature ranging from about 50° C. to about 100° C.

17. The process in accordance with claim 1, wherein said reaction mixture is heated to a temperature ranging from about 60° C. to about 75° C.

18. The process in accordance with claim 7, wherein said compound of Formula I has the following general formula:

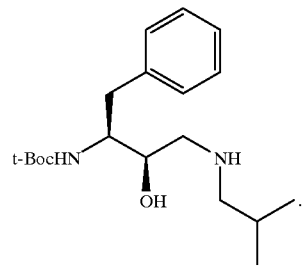

19. The process in accordance with claim 1, wherein said compound of Formula I is recovered from said reaction mixture by filtration of said compound of Formula I and drying said compound of Formula I.

* * * * *